United States Patent [19]

Burns

[11] 4,388,925

[45] Jun. 21, 1983

[54] AUTOMATIC RETRACTABLE LANCET ASSEMBLY

[75] Inventor: James A. Burns, Elizabeth, N.J.

[73] Assignee: Becton Dickinson and Company, Paramus, N.J.

[21] Appl. No.: 246,523

[22] Filed: Mar. 23, 1981

[51] Int. Cl.³ ............................................. A61B 17/34
[52] U.S. Cl. ................................ 128/314; 128/329 R
[58] Field of Search ................... 128/314, 315, 329 R, 128/329 A, 330, 638, 218 A, 218 F, 253, 770

[56] References Cited

U.S. PATENT DOCUMENTS

| | | | |
|---|---|---|---|
| 55,620 | 6/1866 | Capewell | 128/329 R |
| 1,135,465 | 4/1915 | Pollock | 128/314 |
| 3,030,959 | 4/1962 | Grunert | 128/329 R |
| 4,120,303 | 10/1978 | Villa-Massone et al. | 128/330 |
| 4,139,011 | 2/1979 | Benoit et al. | 128/329 R |
| 4,185,635 | 1/1980 | Burford et al. | 128/330 |
| 4,203,446 | 5/1980 | Hofert et al. | 128/329 R |

FOREIGN PATENT DOCUMENTS 124247  3/1949  Sweden ........................... 128/329 R

OTHER PUBLICATIONS

Sutor et al., "Bleeding from Standardized Skin Punctures", A. J.C.P., vol. 55, May 1971.

Primary Examiner—Michael H. Thaler

[57] ABSTRACT

An automatic retractable lancet assembly includes a housing with a sharp-pointed lancet movably mounted therein. A depressible plunger and slide mechanism actuates the movement of the lancet outwardly from the housing. After this outward movement is completed, the actuator elements become dissociated from further movement of the lancet. Subsequently, the lancet is automatically retracted back inside the housing by virtue of a spring element.

9 Claims, 9 Drawing Figures

U.S. Patent  Jun. 21, 1983  Sheet 3 of 3  4,388,925
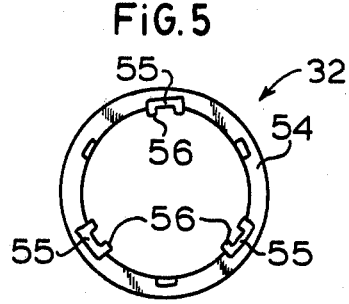
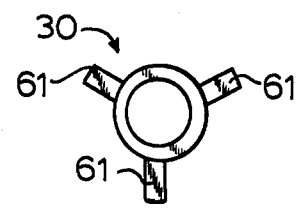
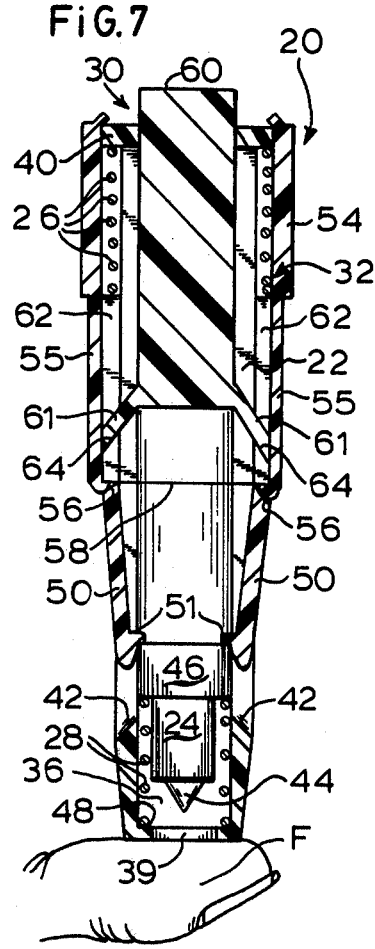
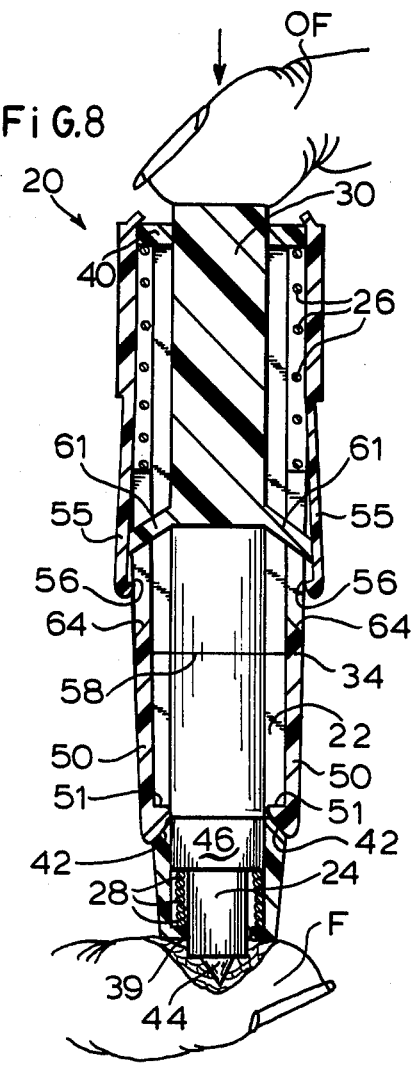

AUTOMATIC RETRACTABLE LANCET ASSEMBLY

BACKGROUND OF THE INVENTION

1. Field of the Invention

The present invention relates to a lancet assembly, and more particularly, concerns an automatic retractable lancet assembly useful in penetrating the skin of a patient.

2. Description of the Prior Art

Sharp-pointed lancets are employed to make a quick puncture or penetration of the patient's skin in order to provide a small outflow of blood. Various tests may be employed with only small amounts of blood so that the blood flowing from a finger prick is normally sufficient. However, due to the sensitive nerve endings in the finger tip area, this procedure could induce a significant amount of pain in the patient even though the skin puncture produces minimal cutting. In order to minimize potential pain, it is desirable to make the thrust of the lancet through the patient's skin rapidly.

Spring-loaded lancets of different types and forms have been well known and are typified, for example, by U.S. Pat. Nos. 55,620; 1,135,465; 3,030,959; 4,139,011; 4,203,446; 4,230,118; Swedish Patent No. 124247 and Sutor, A. H., et al., "Bleeding From Standardized Skin Punctures: Automated Technique for Recording Time, Intensity and Pattern of Bleeding," A. J. C. P., Volume 55, May 1971.

U.S. Pat. No. 4,203,446, above, is significant in that it teaches the puncture of the skin of a patient with a lancet which is retracted back into the device after piercing the patient's skin. In the patented device, the downward motion of the lancet is initiated by the impact of a spring-loaded hammer, and as this motion continues, the spring potential decreases. At the time of impact, the return spring begins to compress and increase potential energy. When the potential energy in the return spring under compression exceeds the potential energy in the driving spring, compression of the return spring ends and decompression begins. This, then, reverses the motion of the lancet. However, impact is necessary to compress the return spring and increase its potential energy rapidly. Without the impact force, the spring forces would approach equilibrium and then there would be no reverse motion in order to retract the lancet out of the patient's skin. Furthermore, since spring potential is critical in this patented device, a conical spring is relied upon to overcome recoil due to the surge of the larger return spring. Despite the foregoing inventions, improvements in this field of lancets are still being sought.

SUMMARY OF THE INVENTION

An automatic retractable lancet assembly of the present invention comprises a housing with a sharp-pointed lancet movably mounted therein. Actuating means moves the lancet outwardly from the housing and thereafter becomes dissociated from further movement of the lancet. Subsequent to this outward movement of the lancet, operable means is provided for automatically retracting the lancet back inside the housing.

In the preferred embodiment of the present invention, the housing includes an aperture with the lancet mounted in the housing so that its point lies adjacent the interior side of the aperture. A depressible plunger is movably mounted in the housing in the end thereof opposite from the lancet. Also mounted inside the housing is a first spring in a compressed condition adapted to decompress upon the plunger being depressed into the housing. This causes the movement of the lancet outward of the aperture for penetration of the skin of a patient. The first spring is adapted to become dissociated from the lancet after the lancet completes its outward movement. A second spring is mounted inside the housing in a substantially decompressed condition before the plunger is depressed. This second spring is adapted to become compressed during outward movement of the lancet. Furthermore, the second spring is adapted to decompress when the first spring becomes dissociated from the lancet. This causes the lancet to be automatically retracted back inside the housing.

In accordance with the principles of the present invention, the desired functions are achieved by virtue of structure which is notably different from the structure of prior art lancet assemblies. In particular, and in the preferable embodiment, two springs are employed to complete the intended purpose of the lancet. The first spring serves as a driving spring to rapidly thrust the lancet outwardly for penetration of the patient's skin. At this time, this driving spring becomes dissociated from movement of the lancet. The second spring serves as a return spring, operable after the driving spring has become so dissociated. Therefore, when the second or return spring automatically retracts the lancet back into the housing, there is no opposing spring force, such as found in U.S. Pat. No. 4,203,446. Thus, in the present invention, the various spring potential energies do not have to balance as in the aforementioned patented invention. The return spring of the present invention only has to be sufficiently strong to retract the lancet inwardly. Therefore, considerations of balancing spring forces, as in the previous inventions, have been obviated by the structure of the present invention. This allows the design of the present invention to include a greater liberality as far as spring sizes and strengths are concerned. Advantageously, the present invention provides a quick thrust of the lancet outwardly to penetrate the skin of the patient, and then automatically retracts the lancet from the patient's skin so that dwell time therein is minimized. It is intended that this embodiment of the present invention can be economically fabricated so that it can be discarded after single use in disposable fashion.

BRIEF DESCRIPTION OF THE DRAWINGS

FIG. 3 is an enlarged end view of the slidable sleeve element taken along line 3—3 of FIG. 2;

FIG. 4 is an enlarged end view of the slidable sleeve element taken along line 4—4 of FIG. 2;

FIG. 5 is an enlarged end view of the skirt element of the preferred invention taken along line 5—5 of FIG. 2;

FIG. 6 is an enlarged end view of the depressible plunger element of the preferred invention taken along line 6—6 of FIG. 2;

FIG. 7 is a cross-sectional view of the automatic retractable lancet assembly taken along line 7—7 of FIG. 1 illustrated in position in conjunction with a finger of a patient;

FIG. 8 is a cross-sectional view of the lancet assembly of FIG. 7 illustrating the sequential operation of the assembly to penetrate the finger of the patient; and FIG. 9 is a cross-sectional view of the lancet assembly of FIGS. 7 and 8 illustrating the next sequential operative step after the lancet has been automatically retracted back into the assembly after the finger of the patient has been penetrated.

DETAILED DESCRIPTION

Figure 1:
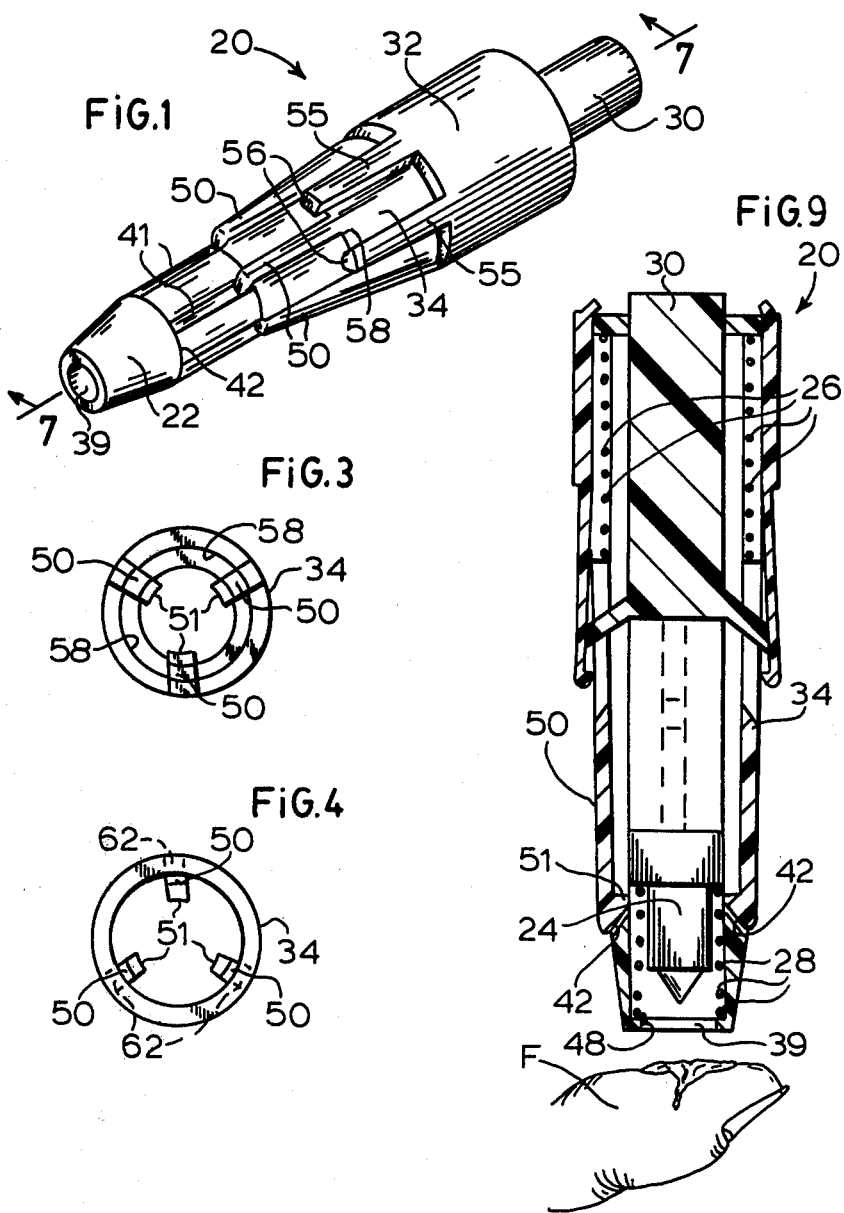
FIG. 1 is a perspective view illustrating the preferred embodiment of the automatic retractable lancet assembly of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
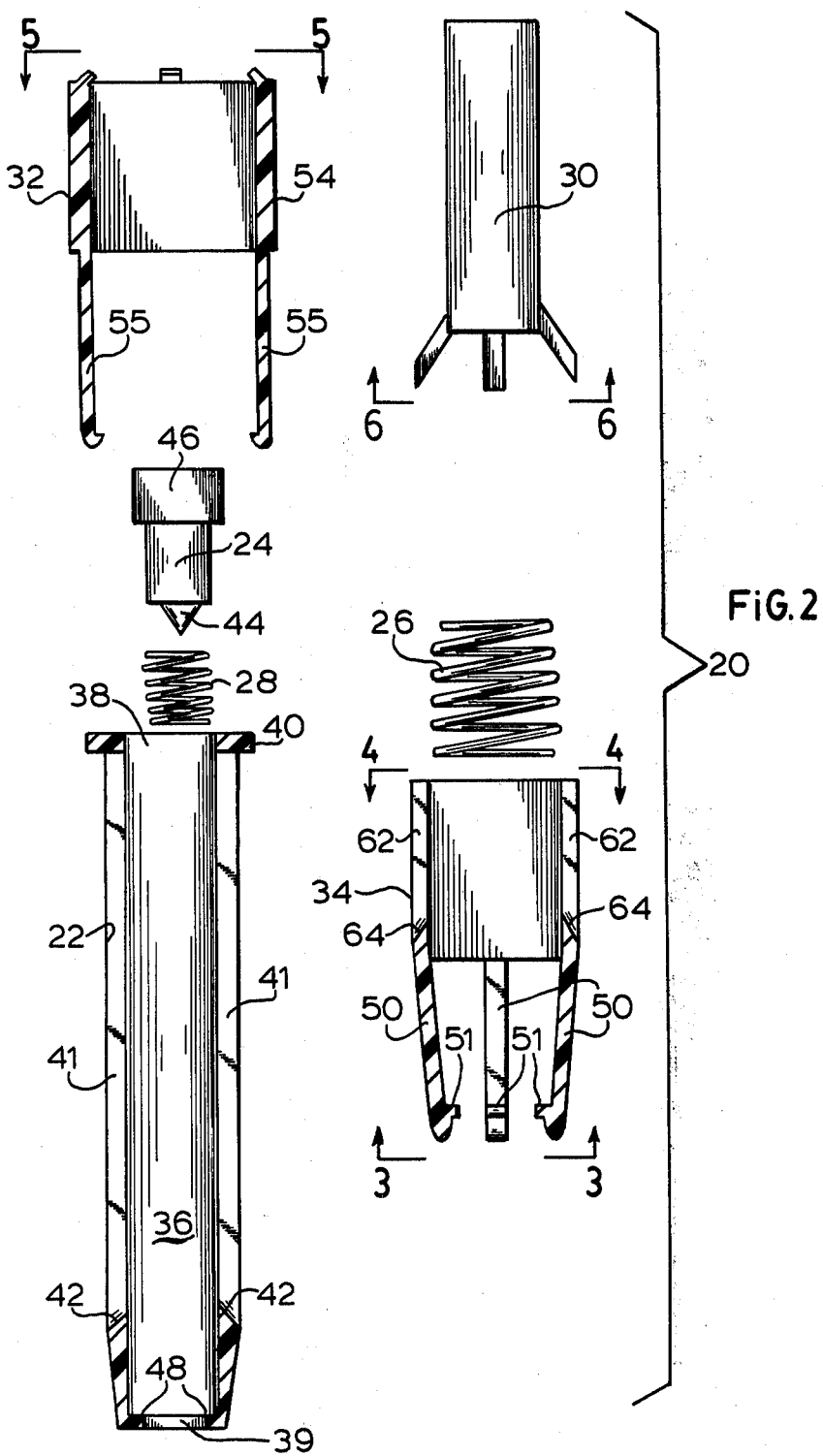
FIG. 2 is an exploded assembly plan view of the elements of the automatic retractable lancet assembly of FIG. 1.

Referring to the drawings, and FIGS. 1 and 2 in particular, there is illustrated a preferred embodiment of an automatic retractable lancet assembly 20. As more clearly seen in FIG. 2, taken in conjunction with FIG. 1, the basic components of lancet assembly 20 are the following: a housing 22, a lancet 24, a first spring 26, a second spring 28, a depressible plunger 30, a skirt 32 and a slidable sleeve 34. In this embodiment being described, all of the aforementioned elements are preferably cylindrically shaped and designed for coaxial arrangement with each other as described below.

More specifically, housing 22 is an elongate hollow tube having a passageway 36 therethrough terminating in an opening 38 at its proximal end and an aperture 39 at its distal end. An annular flange 40 surrounds opening 38 for structural purposes in maintaining the elements together when assembled. In this particular embodiment, there are three longitudinal slots 41 (only two being shown in FIG. 2 since they are spaced approximately 120° apart) through the peripheral wall of housing 22. These slots terminate toward the distal end of the housing at slanted, inclined surfaces 42.

Lancet 24 includes a sharp point 44 extending from a slidable piston 46. As more clearly seen in FIG. 7 which represents the instant invention in the assembled condition before use, lancet 24 is slidably positioned inside passageway 36. The diameter of piston 46 is designed to slide within the inside diameter of passageway 36 of housing 22. Sharp point 44 faces toward aperture 39 and is maintained inside the housing adjacent the interior side of aperture 39. Second spring 28 is provided to maintain the lancet in this position. Spring 28 is basically a coil spring which fits around the sharp point of the lancet so that piston 46 rests upon this spring. An inwardly projecting lip 48 at the distal end of the housing 22 cooperates to hold the spring inside the housing. In this position as seen in FIG. 7, which represents the lancet assembly before use, spring 28 is in a substantially decompressed condition.

Slidable sleeve 34 is adapted to slide over housing 22 in coaxial fashion. This sleeve includes three flexible legs 50 spaced approximately 120° apart, as illustrated in FIGS. 3 and 4, and adapted to correspond to slots 41 of the housing. Each flexible leg includes an inwardly projecting foot 51 which projects through corresponding slot 41 in the housing. As seen in FIG. 7, feet 51 engage the top of piston 46 of the lancet. This engagement helps maintain the lancet in a relatively immobile position in the pre-use condition.

Skirt 32, also preferably cylindrically shaped, includes an upper portion 54 which is sized to snugly fit around flange 40 of the housing. The bottom portion of skirt 32 includes three flexible arms 55 extending downwardly, as seen in FIG. 5. Each arm 55 has at its distal end a hook 56 projecting inwardly. In the assembled condition as seen in FIG. 7, skirt 32 is oriented so that arms 55 are peripherally offset from legs 50 of the slidable sleeve. In this manner, hooks 56 fit between legs 50 and engage the flat surfaces 58 on the sleeve between the legs. This immobilizes slidable sleeve in a relatively fixed condition before the lancet assembly is used. In this condition, first spring 26 is compressed between the proximal end of slidable sleeve 34 and flange 40 of the housing. First spring 26 is essentially similar to second spring 28 inasmuch as it is a coil spring. This first spring is, however, larger in diameter and should be designed with a larger spring force inasmuch as it is the driving spring for rapidly thrusting the lancet through the skin of the patient. With the hooks 56 at the end of the skirt 32 engaging the flat surfaces of the slidable sleeve 34, first spring 26 is effectively maintained in the compressed condition before use of this lancet assembly, as more clearly seen by referring to FIG. 7.

Depressible plunger 30 is preferably a cylindrically shaped plug with a flat push-button surface 60 at its proximal end. Depending from the distal end of plunger 30 are three equally spaced flexible arms 61, as illustrated in FIG. 6. Plunger 30 is slidably positioned inside housing 22 in the end opposite from the lancet so that flexible arms 61 project through slots 41 running along the longitudinal axis of the housing. In addition, flexible arms 61 also project through slots 62 which run longitudinally in the proximal portion of slidable sleeve 34 as illustrated in FIG. 4. Slots 62 are oriented to correspond with the orientation of slots 41 in the housing. Slots 62 terminate distally in slanted, inclined surfaces 64 which can be seen in FIG. 7. In the loaded condition before use, flexible arms 61 of the plunger may either contact inclined surfaces 64 or be slightly spaced therefrom. In either case, the flexible arms of the plunger are adapted to engage the inclined surfaces on the slidable sleeve when the plunger is downwardly depressed. FIGS. 1 and 7 illustrate the automatic retractable lancet assembly of the present invention in the loaded condition as it would appear before use. In FIG. 7, a finger F of the patient is positioned adjacent the distal end of the assembly just before use so that the finger covers aperture 39. The operation of this lancet assembly, illustrating penetration of the skin of the finger and then automatic retraction of the lancet is seen in FIGS. 8 and 9.

Turning to FIG. 8, in particular, lancet assembly 20 is shown in position on top of finger F of a patient, while the finger of the operator OF is illustrated pushing downwardly on depressible plunger 30. This downward movement causes flexible arms 61 of the plunger to engage inclined surfaces 64 on the slidable sleeve. Inasmuch as hooks 56 of the skirt maintain the slidable sleeve in a fixed position, contact of flexible arms 61 against inclined surfaces 64 causes the arms to flex outwardly. This outward flexure causes contact with flexible arms 55 of the skirt. In turn, flexible arms 55 flex outwardly a sufficient amount so that hooks 56, at the end of flexible arms 55, become disengaged from flat surfaces 58 on the slidable sleeve. Once this disengagement occurs, there is no force tending to compress spring 26 into the compressed condition. As a result, with the restraining force removed, the spring is released causing an expansion of the spring. This expansion causes sleeve 34 to move distally within housing 22 in a rapid thrusting movement. Inasmuch as feet 51 at the distal end of the sleeve are in engagement with the piston portion of lancet 24, the lancet also moves distally. Sharp point 44 moves rapidly out of aperture 39 and penetrates finger F positioned just under the aperture. While this is occurring, it is noted that the distal movement of lancet 24 has caused second spring 28 to become compressed. This compression is a direct result of the energy transmitted to slidable sleeve 34 by the release of first spring 26. In order to assure proper compression of second spring 28, it is desirable that the first or driving spring have a higher spring constant than the second or return spring.

In addition to causing downward movement of lancet 24 and compression of second spring 28, the downward or distal movement of slidable sleeve 34 causes flexible legs 50 to engage inclined surfaces 42 on housing 22. As a result, the downward movement of flexible legs 50 against inclined surfaces 42 causes these flexible legs to flex outwardly. As a consequence, inwardly projecting feet 51 become disengaged from the piston portion of lancet 24. This condition is more clearly seen by referring to FIG. 9. Inasmuch as feet 51 serve as the restraining force against second spring 28 when compressed, the disengagement of these feet from the lancet effects a release of this spring. This in turn causes an expansion of spring 28 thereby rapidly retracting lancet 24 back inside the housing. It is noted that when spring 28 expands its entire energy is transmitted only to lancet 24 to effect its retraction back inside the housing. With feet 51 disengaged, slidable sleeve 34 also becomes dissociated from the retraction movement of the lancet caused by expansion of second spring 28. Therefore, when second spring 28 expands, it is not working against the decompressed state of first spring 26 since the disengagement of feet 51 dissociate the entire slidable sleeve and first spring 26 from the retraction movement of the lancet and the decompression of second spring 28. Accordingly, with a low amount of energy required to retract the lancet back inside the housing, second spring 28 can be a small, lightweight and inexpensive spring. It is appreciated that the structure of the present lancet assembly causes not only the rapid thrusting movement of the lancet to penetrate the skin of the patient, but also effects the automatic retraction of the lancet back inside the housing of the assembly. Thus, downward depression of plunger 30 is the stimulus for both outward release and inward retraction of the lancet. Insofar as a preferred embodiment of the present invention is intended to be disposable, the housing, slidable sleeve, flexible skirt and depressible plunger can be fabricated of inexpensive plastic materials. On the other hand, lightweight metals can be employed for the lancet and the two springs described above.

Thus, there has been provided in accordance with the present invention an automatic retractable lancet assembly. While two springs are preferably employed, the return spring operates independently and dissociated from any movement of the driving spring. Accordingly, balance of spring forces is not required as in prior art lancet assemblies. This allows more straightforward operation, reduction of spring sizes and lighter weight materials.

What is claimed is:

1. An automatically retractable spring lancet assembly for piercing human skin which assembly includes automatic release of the drive spring for retraction, characterized by
 (a) a housing having an aperture;
 (b) a plurality of elongate openings in said housing;
 (c) a lancet mounted in said housing for reciprocable movement therein;
 (d) a point on said lancet positioned adjacent the interior side of said housing aperture;
 (e) a depressable plunger mounted for reciprocation in said housing in the end thereof opposite said housing aperture;
 (f) the outer end of said plunger extending out of said housing for engagement;
 (g) a sleeve slidable on said housing and positioned to engage said lancet in the piercing forward movement thereof;
 (h) a first compressed spring extending between said housing and said sleeve for the piercing forward movement of said lancet upon engagement of said plunger;
 (i) a second uncompressed spring extending between said lancet and said housing for the compression thereof and automatic retraction of said lancet after the said piercing forward movement thereof;
 (j) cooperating means extending between said plunger and said housing for automatically disengaging said first spring from said lancet after said lancet completes its piercing movement for allowing the automatic retraction of said lancet back through said housing aperture;
 (k) a flexible skirt positioned on said housing for maintaining said sleeve in position for compressing said first spring; and
 (l) a plurality of flexible arms adapted to flex outwardly upon depression of said plunger and contact said flexible skirt and cause said skirt to flex outwardly to thereby become disengaged from said sleeve thereby releasing the restraining force applied to said first spring so that said sleeve moves forward to cause the said forward piercing movement of said lancet.

2. The assembly of claim 1 wherein said sleeve is positioned to restrain said first spring in a compressed condition before said plunger is depressed.

3. The assembly of claim 1 wherein said sleeve includes a plurality of inclined surfaces adapted to be engaged by said plunger flexible arms upon depression of said plunger for causing said flexible arms to flex outwardly.

4. The assembly of claim 1 wherein said housing includes a plurality of longitudinally extending openings circumferentially spaced around its periphery and said sleeve includes a plurality of feet with one each extending through one of said openings for engaging said lancet.

5. The assembly of claim 4 wherein said feet are included on a plurality of flexible legs on said sleeve, said legs adapted to flex outwardly upon distal movement of said sleeve whereby said feet become disengaged from said lancet after said second spring has become compressed, said disengagement of said feet thereby releasing the restraining force applied to said second spring so that said second spring becomes decompressed and thereby automatically retracts said lancet back inside said housing.

6. The assembly of claim 5 wherein said housing includes a plurality of inclined surfaces adapted to be engaged by said flexible legs upon distal movement of said sleeve for causing said legs to flex outwardly.

7. The assembly of claim 1 wherein said housing and said plunger are made of plastic and said lancet is made of metal.

8. The assembly of claim 1, further characterized by
(a) said housing, said plunger and said lancet are cylindrical and coaxial.

9. An automatic retractable lancet assembly comprising:

a substantially cylindrical housing having an aperture;

a sharp-pointed lancet movably mounted in said housing with its point lying adjacent the interior side of said aperture;

a depressible plunger coaxially mounted inside said housing in the end thereof opposite from said lancet including a plurality of flexible arms adapted to flex outwardly upon depression of said plunger;

a first spring mounted inside said housing restrained in a compressed condition, before said plunger is depressed, by a slidable sleeve positioned on said housing, said sleeve including a plurality of flexible legs each having a projecting foot thereon for engaging said lancet;

a flexible skirt positioned on said housing for maintaining the sleeve in position for compressing said first spring and adapted to flex outwardly upon the outward flexing of said plunger arms so that said skirt becomes disengaged from said sleeve to release the restraining force applied to said first spring causing said sleeve to move distally and thereby move said lancet outwardly from said housing; and a second spring mounted inside said housing in a substantially decompressed condition before said plunger is depressed said second spring adapted to become compressed after said sleeve moves distally and causes outward movement of said lancet, said flexible legs of said sleeve adapted to flex outwardly after distal movement of said sleeve whereby said feet become disengaged from said lancet after said second spring has become compressed, said disengagement of said feet thereby releasing the restraining force applied to said second spring so that said second spring becomes decompressed and thereby automatically retracts said lancet back inside said housing.

* * * * *